US009968592B2

(12) United States Patent
Inokuchi et al.

(10) Patent No.: US 9,968,592 B2
(45) Date of Patent: May 15, 2018

(54) DYSLIPIDEMIA THERAPEUTIC AGENT

(71) Applicant: KOWA COMPANY, LTD., Nagoya-shi, Aichi (JP)

(72) Inventors: Yuta Inokuchi, Higashimurayama (JP); Haruki Shibata, Higashimurayama (JP); Toshiaki Takizawa, Higashimurayama (JP)

(73) Assignee: KOWA COMPANY, LTD., Nagoya-shi (JP)

( * ) Notice: Subject to any disclaimer, the term of this patent is extended or adjusted under 35 U.S.C. 154(b) by 0 days. days.

(21) Appl. No.: 15/513,277

(22) PCT Filed: Sep. 28, 2015

(86) PCT No.: PCT/JP2015/077234
§ 371 (c)(1),
(2) Date: Mar. 22, 2017

(87) PCT Pub. No.: WO2016/047799
PCT Pub. Date: Mar. 31, 2016

(65) Prior Publication Data
US 2017/0304273 A1 Oct. 26, 2017

(30) Foreign Application Priority Data
Sep. 26, 2014 (JP) .................................. 2014-196001

(51) Int. Cl.
*A61K 31/423* (2006.01)
*A61K 31/4152* (2006.01)
*A61K 45/06* (2006.01)
*A61K 45/00* (2006.01)

(52) U.S. Cl.
CPC ........ *A61K 31/423* (2013.01); *A61K 31/4152* (2013.01); *A61K 45/06* (2013.01); *A61K 45/00* (2013.01); *A61K 2300/00* (2013.01)

(58) Field of Classification Search
CPC .. A61K 31/423; A61K 31/4152; A61K 45/06; A61K 45/00; A61K 2300/00
See application file for complete search history.

(56) References Cited

U.S. PATENT DOCUMENTS

| | | | |
|---|---|---|---|
| 9,572,798 B2 * | 2/2017 | Takizawa | A61K 45/06 |
| 9,682,942 B2 * | 6/2017 | Yamazaki | C07D 239/47 |
| 2003/0125316 A1 | 7/2003 | Keller et al. | |
| 2005/0101636 A1 | 5/2005 | Yamazaki et al. | |
| 2013/0225618 A1 * | 8/2013 | Shibuya | A61K 31/505 514/272 |
| 2014/0134262 A1 | 5/2014 | Arai et al. | |
| 2015/0196538 A1 * | 7/2015 | Takizawa | A61K 45/06 514/210.02 |
| 2016/0031827 A1 * | 2/2016 | Yamazaki | C07D 239/47 514/272 |
| 2016/0136138 A1 * | 5/2016 | Shibata | A61K 31/423 514/375 |
| 2016/0206598 A1 * | 7/2016 | Takizawa | A61K 31/202 |
| 2017/0112811 A1 * | 4/2017 | Takizawa | A61K 45/06 |
| 2017/0252338 A1 * | 9/2017 | Shibata | A61K 45/00 |

FOREIGN PATENT DOCUMENTS

| | | |
|---|---|---|
| EP | 1 661 890 A1 | 5/2006 |
| EP | 1661890 B1 | 5/2006 |
| EP | 2 578 574 A1 | 4/2013 |
| JP | 2002-533410 A | 10/2002 |
| JP | 2014-520795 A | 8/2014 |
| WO | 2000/038724 A1 | 7/2000 |
| WO | 2005/023777 A1 | 3/2005 |
| WO | 2011/002696 A1 | 1/2011 |

OTHER PUBLICATIONS

A. Otocka-Kmiecik et al., 51 Progress in Lipid Research, 314-324 (2012).*
R.M. Stoekenbroek et al., 13 BCM Medicine 1-6 (2015).*
International Search Report dated Dec. 28, 2015, issued in counterpart application No. PCT/JP2015/077234. (2 pages).
Tanimoto, "Research and developmental strategy of anti-dyslipidemic agents.", Folia Pharmacal. Jpn., 2007, vol. 129, pp. 267-270, w/ English translation (12 pages).
Schoonjans et al., "Role of the peroxisome proliferator-activated receptor (PPAR) in mediating the effects of fibrates and fatty acids on gene expression", Journal of Lipid Research, 1996, vol. 37, pp. 907-925 (19 pages).
Barbier et al., "Genomic and non-genomic interactions of PPARα with xenobiotic-metabolizing enzymes", Trends in Endocrinology and Metabolism, Sep. 2004, vol. 15, No. 7, pp. 324-330 (7 pages).
Miyares et al., "Patient considerations and clinical impact of cholesteryl ester transfer protein inhibitors in the management of dyslipidemia: focus on anacetrapib", Vascular Health and Risk Management, 2012, vol. 8, pp. 483-493 (11 pages).
Extended (supplementary) European Search Report dated Jan. 30, 2018, issued in counterpart European Application No. 15844904.1. (6 pages).
Notification of Transmittal of Translation of the International Preliminary Report on Patentability (Form PCT/IB/338) issued in counterpart International Application No. PCT/JP2015/077234 dated Apr. 6, 2017, with Forms PCT/IB/373, PCT/ISA/237 and PCT/IB/326. (14 pages).

* cited by examiner

*Primary Examiner* — Alexander R Pagano
(74) *Attorney, Agent, or Firm* — Westerman, Hattori, Daniels & Adrian, LLP

(57) ABSTRACT

This invention provides a combination-drug composition and a combination use of pharmaceuticals for preventing and/or treating dyslipidemic conditions such as hyper-LDL cholesterolemia in mammals, including humans.
This invention pertains to a drug composition for preventing and/or treating dyslipidemia and the like, the drug composition including the following: (R)-2-[3-[[N-(benzoxazol-2-yl)-N-3-(4-methoxyphenoxy)propyl]aminomethyl]phenoxy] butyric acid, a salt thereof, or a solvate of either; and (S)-trans-{4-[({2-[({1-[3,5-bis(trifluoromethyl)phenyl]ethyl}{5-[2-(methyl sulfonyl)ethoxy]pyrimidin-2-yl}amino)methyl]-4-(trifluoromethyl)phenyl}(ethyl)amino)methyl]cyclohexyl} acetic acid, a salt thereof, or a solvate of either.

6 Claims, 1 Drawing Sheet

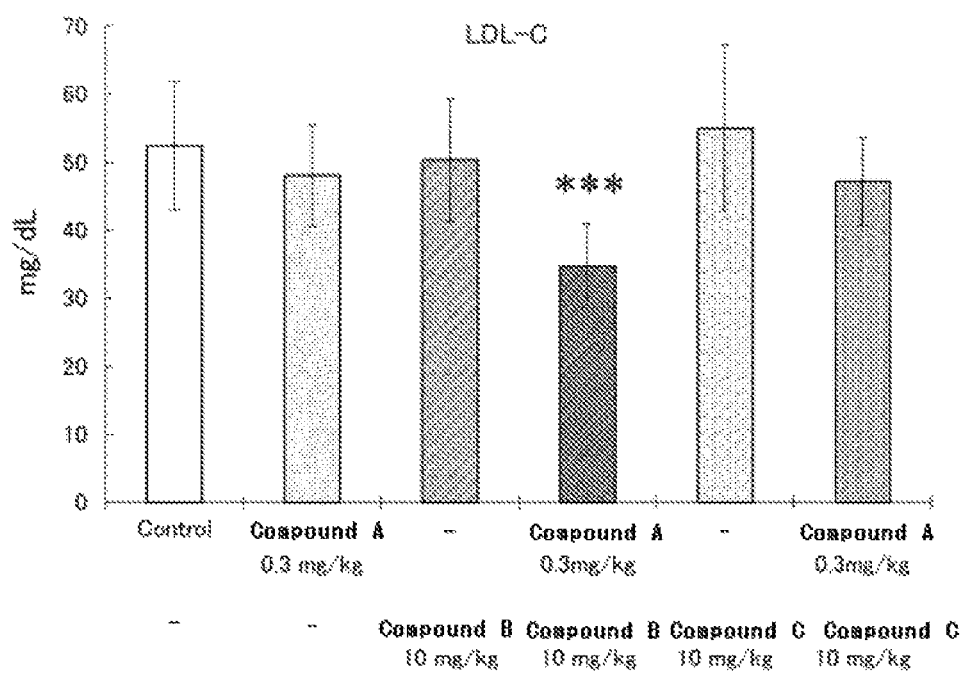

DYSLIPIDEMIA THERAPEUTIC AGENT

TECHNICAL FIELD

The present invention relates to a composition containing (R)-2-[3-[[N-(benzoxazol-2-yl)-N-3-(4-methoxyphenoxy) propyl]aminomethyl]phenoxy] butyric acid and (S)-trans-{4-[([2-[({1-[3,5-bis(trifluoromethyl)phenyl] ethyl}{5-[2-(methylsulfonyl)ethoxy]pyrimidin-2-yl}amino)methyl]-4-(trifluoromethyl)phenyl}(ethyl) amino)methyl]cyclohexyl} acetic acid, and combination use thereof for preventing and/or treating dyslipidemic conditions such as atherosclerosis or hypercholesterolemia.

BACKGROUND ART

In recent years, due to westernization of food, patients with hypercholesterolemia, hypertriglyceridemia, hypo HDL cholesterolemia, or the like, which are in a category of so-called lifestyle-related diseases have been increasing. In addition, recently, patients with mixed or combined dyslipidemia with both hypercholesterolemia and hypertriglyceridemia have been increasing. Particularly, patients of mixed dyslipidemia have LDL cholesterol (LDL-C) and triglyceride (TG) raised, and have HDL cholesterol (HDL-C) lowered. Such a high TG and low HDL-C condition is observed also in patients with metabolic syndrome or diabetes. It has been proven that hyper LDL chelesterolemia, hypo HDL cholesterolemia, and hypertriglyceridemia are risk factors of a coronary artery disease (CAD), a cerebrovascular disorder, or the like. The importance of the management of dyslipidemia is described in "Guidelines for Prevention of Atherosclerotic Cardiovascular Diseases 2012" released by Japan Atherosclerosis Society.

Dyslipidemia, particularly hypercholesterolemia has become a disease having a quite high degree of medical satisfaction due to advent of statins. However, from results of many large-scale clinical trials, it has been found that further lowering of LDL cholesterol in blood leads to prevention of coronary artery diseases (the lower, the better). More strict lipid control has been recommended. Many patients cannot reach the intended LDL-C level in blood only with statins. Combination use of multiple pharmaceutical agents has been also required (Non-Patent Document 1).

PPAR is one of receptors belonging to a nuclear receptor family. Existence of three subtypes (α, γ, and δ) is known for this receptor (Non-Patent Document 2). Among these types, PPARα is mainly expressed in the liver. When PPARα is activated, production of apo C-III is suppressed, followed by activation of lipoprotein lipase (LPL). As a result, fat is decomposed. As PPARα agonist, for example, unsaturated fatty acids and fibrate pharmaceutical agents such as fenofibrate, bezafibrate, or gemfibrozil have been known (Non-Patent Document 3). In recent years, a compound having a stronger and more selective PPARα activating effect than a conventional fibrate pharmaceutical agent has been reported (Patent Document 1).

A cholesterol ester transfer protein (CETP) is a glycoprotein having strong hydrophobicity and having a molecular weight of 68,000 to 74,000, primarily produced in the liver and small intestine, and transfers a cholesterol ester in a high density lipoprotein (HDL) to a very low density lipoprotein (VLDL) or a low density lipoprotein (LDL). Therefore, it has been reported that a CETP inhibitor typified by Anacetrapib ([4S,5R]-5-[3,5-bis(trifluoromethyl)phenyl]-3-{[4'-fluoro-2'-methoxy-5'-(propan-2-yl)-4-(trifluoromethyl)[1,1'-biphenyl]-2-yl]methyl}-4-methyl-1,3-oxazolidin-2-one (Non-Patent Document 5), hereinafter, also referred to as compound C) or Evacetrapib (Patent Document 2) suppresses cholesterol transfer from HDL to LDL to reduce LDL-C (Non-Patent Document 4).

Under such circumstances, Patent Document 3 has made a report on a combination-drug of fibric acid derivatives and CETP inhibitors. This Patent Document describes a method for treating a cardiovascular disease, specifically describes that this combination-drug can be used for medical science, particularly for atherosclerosis, hypercholesterolemia, other coronary artery diseases, and the like in mammals. However, this Document does not describe the combination of compounds of the present invention. Furthermore, the disclosed combinations of fibric acid derivatives and CETP inhibitors do not include any specific experimental example. This Document does not disclose a pharmacological effect due to a combination of multiple pharmaceuticals.

CITATION LIST

Patent Document

Patent Document 1: WO 2005/023777 A1
Patent Document 2: WO 2011/002696 A1
Patent Document 3: WO 2000/038724 A1

Non-Patent Document

Non-Patent Document 1: Journal of Pharmacological Sciences 129, 267-270 (2007)
Non-Patent Document 2: J. Lipid Research, 37, 907-925 (1996)
Non-Patent Document 3: Trends, in Endocrinology and Metabolism, 15(7), 324-330 (2004)
Non-Patent Document 4: Vasc. Health. Risk. Manag., 8, 483-433(2012)

SUMMARY OF THE INVENTION

Problems to be Solved by the Invention

An object of the present invention is to provide a pharmaceutical composition comprising a combination of pharmaceutical agents and combination use of pharmaceutical agents for preventing and/or treating dyslipidemic conditions such as atherosclerosis, hypercholesterolemia, or hyper LDL cholesterolemia.

Means to Solving the Problems

The present inventors made intensive studies in view of these circumstances. As a result, the present inventors have found that a strong effect of lowering LDL cholesterol in blood is exhibited by combination use of (R)-2-[3-[[N-(benzoxazol-2-yl)-N-3-(4-methoxyphenoxy) propyl]aminomethyl]phenoxy]butyric acid (Example 85 in Patent Document 1: hereinafter, also referred to as compound A) reported as a selective PPARα activation agent, and (S)-trans-{4-[({2-[({1-[3,5-bis(trifluoromethyl)phenyl] ethyl}{5-[2-(methylsulfonyl)ethoxy]pyrimidin-2-yl}amino)methyl]-4-(trifluoromethyl)phenyl}(ethyl) amino)methyl]cyclohexyl} acetic acid (hereinafter, also referred to as compound B) which is an optically active substance in Example 45 among compounds reported as CETP inhibitors in WO 2008/129951 A1, and thus have completed the present invention.

That is, the present invention provides a pharmaceutical composition for preventing and/or treating dyslipidemia, comprising a)
(R)-2-[3-[[N-(benzoxazol-2-yl)-N-3-(4-methoxyphenoxy) propyl]aminomethyl]phenoxy] butyric acid, a salt thereof, or a solvate thereof, and b)
(S)-trans-{4-[({2-[({1-[3,5-bis(trifluoromethyl)phenyl] ethyl}{5-[2-(methylsulfonyl)ethoxy]pyrimidin-2-yl}amino)methyl]-4-(trifluoromethyl)phenyl}(ethyl) amino)methyl]cyclohexyl} acetic acid, a salt thereof, or a solvate thereof.

More specifically, the present, invention provides a pharmaceutical composition for preventing and/or treating hyper LDL cholesterolemia, comprising a)
(R)-2-[3-[[N-(benzoxazol-2-yl)-N-3-(4-methoxyphenoxy) propyl]aminomethyl]phenoxy] butyric acid, a salt thereof, or a solvate thereof, and b)
(S)-trans-{4-[({2-[({1-[3,5-bis(trifluoromethyl)phenyl] ethyl}{5-[2-(methylsulfonyl)ethoxy]pyrimidin-2-yl}-amino)methyl]-4-(trifluoromethyl)phenyl}(ethyl) amino}methyl]cyclohexyl} acetic acid, a salt thereof, or a solvate thereof.

More specific description of the present invention is as follows.

(1) A pharmaceutical composition for preventing and/or treating dyslipidemia, comprising
(R)-2-[3-[[N-(benzoxazol-2-yl)-N-3-(4-methoxyphenoxy) propyl]aminomethyl]phenoxy]butyric acid (compound A), a salt thereof, or a solvate of either, and
(S)-trans-{4-[({2-[({1-[3,5-bis(trifluoromethyl)phenyl] ethyl}{5-[2-(methylsulfonyl)ethoxy]pyrimidin-2-yl}amino)methyl]-4-(trifluoromethyl)phenyl}(ethyl) amino)methyl]cyclohexyl} acetic acid (compound B), a salt thereof, or a solvate, of either.

(2) The pharmaceutical composition described in (1), in which the dyslipidemia is hyper LDL cholesterolemia (LDL-C).

(3) The pharmaceutical composition described in (1) or (2), in which a mass ratio between compound A, a salt thereof, or a solvate of either; and compounds, a salt thereof, or a solvate of either; is from 1:1 to 1:10000.

(4) A pharmaceutical composition for lowering LDL cholesterol (LDL-C), comprising compound A, a salt thereof, or a solvate of either, and compound B, a salt thereof, or a solvate of either.

(5) The pharmaceutical composition described in (4), in which a disease requiring lowering of LDL cholesterol (LDL-G) is hyper LDL cholesterolemia (LDL-C).

(6) The pharmaceutical composition described in (4) or (5), in which a mass ratio between compound A, a salt thereof, or a solvate of either; and compounds, a salt thereof, or a solvate of either; is from 1:1 to 1:10000.

(7) A medicine for lowering LDL cholesterol (LDL-C), obtained by combining a pharmaceutical composition comprising compound A, a salt thereof, or a solvate of either, and a pharmaceutically acceptable carrier; and a pharmaceutical composition comprising compound B, a salt thereof, or a solvate of either, and a pharmaceutically acceptable carrier.

(8) medicine described in (7), in which a disease requiring lowering of LDL cholesterol (LDL-C) is hyper LDL cholesterolemia (LDL-C).

(9) The medicine described in (7) or (8), in which a mass ratio between compound A, a salt thereof, or a solvate of either; and compound B, a salt thereof, or a solvate of either; is from 1:1 to 1:10000.

(10) A method for preventing and/or treating dyslipidemia of a patient, comprising: administering an effective amount of a pharmaceutical composition comprising compound A, a salt thereof, or a solvate of either, and compound B, a salt thereof, or a solvate of either to a patient of dyslipidemia or a patient having a risk of suffering from dyslipidemia.

(11) The method described in (10), in which the dyslipidemia is hyper LDL cholesterolemia (LDL-C).

(8) The method for preventing and/or treating dyslipidemia of a patient, described in (10) or (11), in which a mass ratio between compound A, a salt thereof, or a solvate of either, and compound B, a salt thereof, or a solvate of either in the pharmaceutical composition is from 1:1 to 1:10000.

(12) A method for lowering LDL cholesterol (LDL-C) of a patient, comprising: administering an effective amount of a pharmaceutical composition comprising compound A, a salt thereof, or a solvate of either, and compound B, a salt thereof, or a solvate of either to a patient requiring lowering of LDL cholesterol (LDL-C).

(13) The method described in (12), in which a disease requiring lowering of LDL cholesterol (LDL-C) is hyper LDL cholesterolemia (LDL-C).

(14) A pharmaceutical composition for preventing and/or treating dyslipidemia, comprising, as an active ingredient, compound A, a salt thereof, or a solvate of either, which is used in combination with compound B, a salt thereof, or a solvate of either.

(15) The pharmaceutical composition described in (14), in which the dyslipidemia, is hyper LDL cholesterolemia (LDL-C).

(16) The pharmaceutical composition described in (14) or (15), in which a mass ratio between compound A, a salt thereof, or a solvate of either, and compound B, a salt thereof, or a solvate of either is from 1:1 to 1:10000.

(17) A pharmaceutical composition for lowering LDL cholesterol (LDL-C), comprising, as an active ingredient, compound A, a salt thereof, or a solvate of either, which is used in combination with compound B, a salt thereof, or a solvate of either.

(18) The pharmaceutical composition described in (17), in which a disease requiring lowering of LDL cholesterol (LDL-C) is hyper LDL cholesterolemia (LDL-C).

(19) Use of compound A, a salt thereof, or a solvate of either for manufacturing a pharmaceutical composition for preventing and/or treating dyslipidemia by combination use thereof with compound B, a salt thereof, or a solvate of either.

(20) The use described in (19), in which the dyslipidemia is hyper LDL cholesterolemia (LDL-C).

(21) The use described in (19) or (20), in which a mass ratio between compound A, a salt thereof, or a solvate of either, and compound B, a salt thereof, or a solvate of either is from 1:1 to 1:10000.

(22) Use of compound A, a salt thereof, or a solvate of either for manufacturing a pharmaceutical composition for lowering LDL cholesterol (LDL-C) by combination use thereof with compound B, a salt thereof, or a solvate of either.

(23) The use described in (22), in which a disease requiring lowering of LDL cholesterol (LDL-C) is hyper LDL cholesterolemia (LDL-C).

(24) A pharmaceutical composition for preventing and/or treating dyslipidemia, comprising, as an active ingredient, compound B, a salt thereof, or a solvate of either, which is used in combination with a pharmaceutical composition comprising compound A, a salt thereof, or a solvate of either, and a pharmaceutically acceptable carrier.

(25) The pharmaceutical composition described in (24), in which the dyslipidemia is hyper LDL cholesterolemia (LDL-C).

(26) The pharmaceutical composition described in (24) or (25), in which a mass ratio between compound B, a salt, thereof, or a solvate of either, and compound A, a salt, thereof, or a solvate of either is from 1:1 to 10000:1.

(27) A pharmaceutical composition for lowering LDL cholesterol (LDL-C), comprising, as an active ingredient, compound B, a salt, thereof, or a solvate of either, which is used in combination with compound A, a salt, thereof, or a solvate of either.

(28) The pharmaceutical composition described in (27) in which a disease requiring lowering of LDL cholesterol (LDL-C) is hyper LDL cholesterolemia (LDL-C).

(29) Use of compounds, a salt thereof, or a solvate of either for manufacturing a pharmaceutical composition for preventing and/or treating dyslipidemia by combination use thereof with compound A, a salt thereof, or a solvate of either.

(30) The use described in (29), in which the dyslipidemia is hyper LDL cholesterolemia (LDL-C).

(31) The use described in (29) or (30), in which a mass ratio between compound B, a salt thereof, or a solvate of either, and compound A, a salt thereof, or a solvate of either is from 1:1 to 10000:1.

(32) Use of compounds, a salt thereof, or a solvate of either for manufacturing a pharmaceutical composition for lowering LDL cholesterol (LDL-C) by combination use thereof with compound A, a salt thereof, or a solvate of either.

(33) The use described in (32), in which a disease requiring lowering of LDL cholesterol (LDL-C) is hyper LDL cholesterolemia (LDL-C).

Effects of the Invention

The pharmaceutical composition and the medicine according to the present invention exhibit an excellent effect of lowering LDL cholesterol in blood, and are useful for preventing and/or treating dyslipidemia, particularly hyper LDL cholesterolemia.

BRIEF DESCRIPTION OF DRAWINGS

FIG. 1 illustrates LDL-C in plasma at the time of use of compound A (0.3 mg/kg) alone, use of compound B (10 mg/kg) alone, use of compound C (10 mg/kg) alone, combination use of compound A (0.3 mg/kg) and compound B (10 mg/kg), and combination use of compound A (0.3 mg/kg) and compound C (10 mg/kg).

For example, compound A used in the present invention can be produced in accordance with a method described in WO 2005/023777 A1. In addition, compound A can be produced in accordance with a method described in literature.

A chemical structural formula of compound A is as follows.

[Chemical Formula 1]

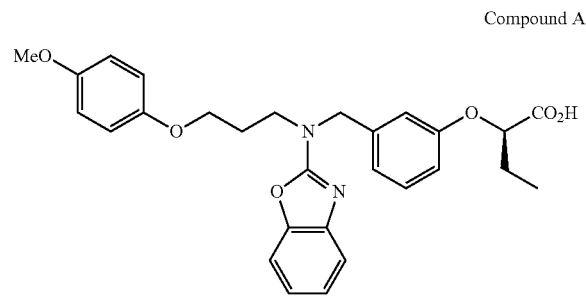

Compound A

In addition, the present invention can use a salt of compound A or a solvate thereof. The salt and the solvate can be manufactured by a usual method.

The salt of compound A is not particularly limited as long as being pharmaceutically acceptable. However, examples thereof include an alkali metal salt such as a sodium salt or a potassium salt; an alkaline earth metal salt such as a calcium salt or a magnesium salt; an organic base salt such as an ammonium salt or a trialkylamine salt; a mineral acid salt such as a hydrochloride or a sulfate; and an organic acid salt such as an acetate.

Examples of the solvate of compound A or a salt thereof include a hydrate and an alcohol solvate (for example, ethanol solvate).

For example, compound B used in the present invention can be produced in accordance with a method described in JP 2013-136572 A1. In addition, compound B can be formulated in accordance with a method described in literature.

A chemical structural formula of compound. B is as follows.

[Chemical Formula 2]

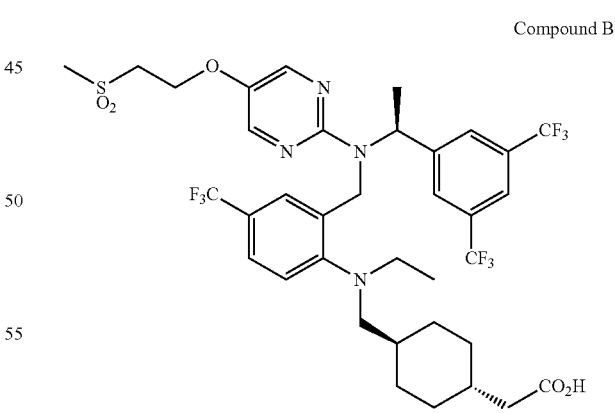

Compound B

In addition, the present invention can use a salt of compound B or a solvate thereof. The salt and the solvate can be manufactured by a usual method.

The salt of compound B is not particularly limited as long as being pharmaceutically acceptable. However, examples thereof include an alkali metal salt such as a sodium salt or a potassium salt; an alkaline earth metal salt such as a calcium salt or a magnesium salt; an organic base salt, such as an ammonium salt or a trialkylamine salt; a mineral acid salt such as a hydrochloride or a sulfate; and an organic acid salt such as an acetate.

Examples of the solvate of compound B or a salt thereof include a hydrate and an alcohol solvate (for example, ethanol solvate).

As described in Examples below, by combination use of compound A, a salt thereof, or a solvate thereof, and compound B, a salt thereof, or a solvate thereof, an effect of lowering LDL-C in plasma was exhibited in an evaluation system using a hamster. Therefore, the pharmaceutical agents of the present invention are useful for preventing and/or treating dyslipidemia such as hypercholesterolemia or hyper LDL cholesterolemia.

When the term dyslipidemia is used here, dyslipidemia means a case where any one of a total triglyceride (TG) level, a total cholesterol (TC) level, a VLDL cholesterol (VLDL-C) level, a LDL cholesterol (LDL-C) level, and a HDL cholesterol (HDL-C) level in blood, or two or more thereof deviate from a range of normal values. A case where the LDL cholesterol (LDL-C) level deviates from a range of normal values is a preferable example or dyslipidemia in the present invention. A disease requiring lowering of LDL cholesterol (LDL-C) in the present invention means a case where the LDL-C level in blood is higher than a normal value.

The pharmaceutical composition of the present invention can be formed into a dosage form such as a tablet, a capsule, a granule, a powder, a lotion, an ointment, an injection, or a suppository singly or using another pharmaceutically acceptable carrier. These formulations can be manufactured by a known method. For example, when a formulation for oral administration is manufactured, the formulation can be manufactured by appropriately combining and formulating a dissolving agent such as gum tragacanth, gum arabic, a sucrose fatty acid ester, lecithin, olive oil, soybean oil, or PEG400; an excipient such as starch, mannitol, or lactose; a binder such as methyl cellulose, sodium carboxymethylcellulose, or hydroxypropylcellulose; a disintegrating agent such as crystalline cellulose or calcium carboxymethylcellulose; a lubricant such as talc or magnesium stearate; and a flow improver such as light anhydrous silicic acid.

As a use form of the pharmaceutical composition of the present invention, it is possible to use a form in which an effect for preventing and/or treating dyslipidemia such as hypercholesterolemia, or hyper LDL cholesterolemia is obtained by combining a) compound A, a salt thereof, or a solvate thereof, and b) compound B, a salt thereof, or a solvate thereof, and by using a synergistic effect for raising HDL-C in blood due to administration of the two pharmaceutical agents in addition to an effect by each of the pharmaceutical agents. However, the use form of the present invention is not limited thereto. Compound A, a salt thereof, or a solvate thereof, and compound B, a salt thereof, or a solvate thereof may be administered simultaneously, or may be administered separately at an interval.

Compound A, a salt thereof, or a solvate thereof, and compound B, a salt thereof, or a solvate thereof may be formulated into a single formulation, or the two pharmaceutical agents may be formulated separately to be used as a kit. That is, the pharmaceutical composition of the present invention may be a kit formed by combining a pharmaceutical agent comprising at least one selected from compound A, a salt thereof, and a solvate thereof as an active ingredient, and a pharmaceutical agent comprising at least one selected from compound B, a salt thereof, and a solvate thereof.

In the present invention, when the two pharmaceutical agents are administered as a single formulation, a blending ratio between compound A, a salt thereof, or a solvate thereof, and compound B, a salt thereof, or a solvate thereof can be appropriately selected in a range of an effective dose of each active ingredient, but in general, is preferably from 1:1 to 1:10000, more preferably from 1:5 to 1:4000, and particularly preferably from 1:10 to 1:1000 in terms of a mass ratio.

When compound A, a salt thereof, or a solvate thereof, and compound B, a salt thereof, or a solvate thereof are formulated separately, dosage forms of the two pharmaceutical agents may be the same as or different from each other. In addition, the numbers of dose for ingredients may be different from one another.

Compound A, a salt thereof, or a solvate thereof of the present invention is administered orally or parenterally. The dose of the pharmaceutical agents of the present invention vary according to a patient's weight, age, sex, symptoms, and the like. However, in a case of an adult, it is usually desirable to administer 0.001 to 100 mg, preferably 0.01 to 10 mg, and particularly preferably 0.1 to 0.4 mg as compound A per day in one to three parts. As for compound B, a salt thereof, or a solvate thereof, it is desirable to administer 0.01 to 1000 mg, preferably 0.1 to 800 mg, and particularly preferably 1 to 400 mg as compound B per day in one to four parts.

EXAMPLES

Hereinafter, the present invention will be described more specifically based on Examples, but the present invention is not limited in any way by the Examples.

Example 1: Effect on LDL-C of Hamster in Combination Use of Compound A and Compound B 1. Method Male hamsters (6-week-old, Slc:Syrian, Japan SLC, Inc.) were used for an experiment. Blood was collected from the jugular vein under satiation. The hamsters were divided into six groups (N=8) based on TG and TC in plasma and a body weight. For two weeks from the next day, each of a solvent (0.5% methylcellulose aqueous solution: MC), compound A alone, compound B alone, and combination of compound A and compound B was orally administered once per day. For comparison, for two weeks, each of compound C alone and combination of compound A and compound C was orally administered once per day. On the final day of administration of the pharmaceutical agent, blood was collected under fasting conditions for four hours and under isoflurane anesthesia, and LDL-C in plasma was measured using high performance liquid chromatography by a method of Usui et al. (Usui S et al. Clin Chem., 46, 63-72, 2000).

2. Group Configuration

Group 1: Control
Group 2: 0.3 mg/kg of compound A
Group 3: 10 mg/kg of compound B
Group 4: 0.3 mg/kg of compound A and 10 mg/kg of compound B
Group 5: 10 mg/kg of compound C
Group 6: 0.3 mg/kg of compound A and 10 mg/kg of compound C 3. Statistical Analysis and Data Processing Method Results were presented by an average value±standard deviation. Comparison between the control group and each of the pharmaceutical agent administration groups was performed by a multiple comparison test of Dunnett, and a risk rate of less than 5% was determined to have a significant difference.

4. Result

FIG. 1 illustrates results of measurement of LDL-C. In single administration of compound A, compound B, or compound C, a clear influence on LDL-C was not observed. However, in a group of combined administration of 0.3 mg/kg of compound A and 10 mg/kg of compound B, significant lowering (***: p<0.001 with respect to control) of LDL-C was observed. In a group of combined administration of 0.3 mg/kg of compound A and 10 mg/kg of compound C, a clear influence on LDL-C was not observed.

These results indicate that combination use of compound A and compound B becomes effective even with a dose with which a therapeutic effect of the pharmaceutical agent is not observed by single administration. That is, it has been indicated that combination use of compound A and compound B which are the pharmaceutical composition and the medicine according to the present invention exhibits a strong action for improving dyslipidemia.

INDUSTRIAL APPLICABILITY

The pharmaceutical composition and the medicine according to the present invention exhibit an excellent effect of lowering LDL-C in blood, are useful for preventing and/or treating dyslipidemia, particularly hyper LDL cholesterolemia, and therefore have industrial applicability.

The invention claimed is:

1. A pharmaceutical composition for preventing and/or treating dyslipidemia, comprising:
   (R)-2-[3-[[N-(benzoxazol-2-yl)-N-3-(4-methoxyphenoxy)propyl]aminomethyl]phenoxy] butyric acid, a salt thereof, or a solvate of either; and
   (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl} acetic acid, a salt thereof, or a solvate of either.

2. The pharmaceutical composition according to claim 1, wherein the dyslipidemia is hyper LDL cholesterolemia.

3. The pharmaceutical composition according to claim 1, wherein a mass ratio between (R)-2-[3-[[N-(benzoxazol-2-yl)-N-3-(4-methoxyphenoxy)propyl]aminomethyl]phenoxy] butyric acid, a salt thereof, or a solvate of either, and (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl} acetic acid, a salt thereof, or a solvate of either is from 1:1 to 1:10000.

4. A medicine for lowering LDL cholesterol, obtained by combining:
   a pharmaceutical composition comprising (R)-2-[3-[[N-(benzoxazol-2-yl)-N-3-(4-methoxyphenoxy)propyl]aminomethyl]phenoxy] butyric acid, a salt thereof, or a solvate of either, and a pharmaceutically acceptable carrier; and
   a pharmaceutical composition comprising (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl} acetic acid, a salt thereof, or a solvate of either, and a pharmaceutically acceptable carrier.

5. The medicine according to claim 4, wherein a disease requiring lowering of LDL-C is hyper LDL cholesterolemia.

6. The medicine according to claim 4, wherein a mass ratio between (R)-2-[3-[[N-(benzoxazol-2-yl)-N-3-(4-methoxyphenoxy)propyl]aminomethyl]phenoxy] butyric acid, a salt thereof, or a solvate of either, and (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl} acetic acid, a salt thereof, or a solvate of either is from 1:1 to 1:10000.

* * * * *